United States Patent
Song et al.

(10) Patent No.: US 12,043,603 B2
(45) Date of Patent: Jul. 23, 2024

(54) METHOD FOR EXTRACTING AND SEPARATING DIHYDROMYRICETIN FROM RATTAN TEA

(71) Applicant: SHANGHAI SPARK PHARMACEUTICAL CO., LTD., Shanghai (CN)

(72) Inventors: Kunyuan Song, Shanghai (CN); Gong Chen, Shanghai (CN); Weiwei Chen, Shanghai (CN); Fang Yan, Shanghai (CN)

(73) Assignee: SHANGHAI SPARK PHARMACEUTICAL CO., LTD., Shanghai (CN)

( * ) Notice: Subject to any disclaimer, the term of this patent is extended or adjusted under 35 U.S.C. 154(b) by 149 days.

(21) Appl. No.: 17/599,823

(22) PCT Filed: May 8, 2020

(86) PCT No.: PCT/CN2020/089148
§ 371 (c)(1),
(2) Date: Sep. 29, 2021

(87) PCT Pub. No.: WO2021/031622
PCT Pub. Date: Feb. 25, 2021

(65) Prior Publication Data
US 2022/0194915 A1 Jun. 23, 2022

(30) Foreign Application Priority Data
Aug. 20, 2019 (CN) .......................... 201910770006.X

(51) Int. Cl.
*C07D 311/40* (2006.01)
*C07D 311/32* (2006.01)

(52) U.S. Cl.
CPC ................................ *C07D 311/40* (2013.01)

(58) Field of Classification Search
CPC .......................... C07D 311/40; C07D 311/32
See application file for complete search history.

(56) References Cited

FOREIGN PATENT DOCUMENTS

| CN | 102225923 A | 10/2011 |
| CN | 106967030 A | 7/2017 |
| CN | 108840849 A | 11/2018 |
| CN | 109053665 | * 12/2018 |
| CN | 110330473 A | 10/2019 |

OTHER PUBLICATIONS

Machine translation of CN109053665, 2023.*

* cited by examiner

*Primary Examiner* — Sun Jae Yoo
(74) *Attorney, Agent, or Firm* — Muncy. Geissler, Olds & Lowe, P.C.

(57) ABSTRACT

A method for extracting and separating dihydromyricetin from rattan tea, which belongs to the technical field of natural medicine extraction and separation, includes: 1) weighing rattan tea leaves, then adding solvent thereto, stirring and refluxing to extract, filtering, keeping on refluxing extraction of residue, and combining extract; 2) adding activated carbon to the extract, performing decolorization, filtering, retaining the filtrate, and then concentrating the filtrate; and 3) crystallizing the concentrated filtrate, filtering, and washing the crystals with cold water and vacuum drying. The method has simple process, high yield and stability, and is easy to realize industrialized production.

6 Claims, 3 Drawing Sheets

analysis report

<Sample Information>

Sample name:

Sample ID:

Data file name: Test sample 1-1, lcd

Method file name: Dihydromyricetin, 1cm

Batch file name: 20180323 Dihydromyricetin sample detection, 1cb

Sample vial number: 1-4  Sample type: unknown

Injection volume: 10 uL

Analysis date: 2018/3/23 15:53:17  Analyst: huyajing

Handling date: 2018/3/23 16:28:19  Handler: huyajung

<Chromatogram>

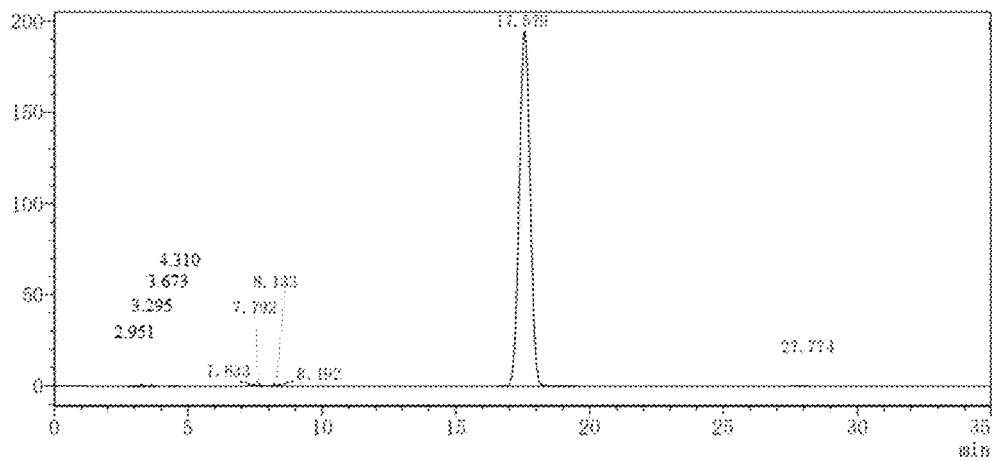

<Peak Table>

Detector A 291nm

| Peak number | Retention time | area | height | theoretical plate number (USP) | Tailing factor | Resolution (USP) | area% |
|---|---|---|---|---|---|---|---|
| 1 | 2.951 | 1018 | 106 | 2453 | 0.776 | --- | 0.018 |
| 2 | 3.295 | 8528 | 758 | 2431 | --- | 1.363 | 0.155 |
| 3 | 3.673 | 3925 | 467 | 5619 | --- | 1.629 | 0.071 |
| 4 | 4.310 | 1353 | 84 | 491 | --- | 1.308 | 0.025 |
| 5 | 7.633 | 1031 | 151 | 123 | --- | 1.884 | 0.019 |
| 6 | 7.792 | 1996 | 180 | 379 | --- | 0.073 | 0.036 |
| 7 | 8.133 | 1095 | 161 | 63 | --- | 0.126 | 0.020 |
| 8 | 8.192 | 2025 | 143 | 68 | --- | 0.014 | 0.037 |
| 9 | 17.579 | 5484975 | 194281 | 8732 | 1.016 | 3.972 | 99.563 |
| 10 | 27.774 | 3086 | 131 | 10345 | --- | 11.053 | 0.056 |
| total | | 5509032 | 196460 | | | | 100.000 |

Dihydromyricetin – 1-47/1-506-1 – Test product 1-1.lcd

FIG. 1

analysis report

<Sample Information>
Sample name:
Sample ID:
Data file name: Test sample 1-1, lcd
Method file name: Dihydromyricetin, 1cm
Batch file name: 20180323 Dihydromyricetin sample detection, 1cb
Sample vial number: 1-18          Sample type: unknown
Injection volume: 10 uL
Analysis date: 2018/3/27 21:30:04     Analyst: huyajing
Handling date: 2018/3/27 22:05:06     Handler: huyajung
<Chromatogram>

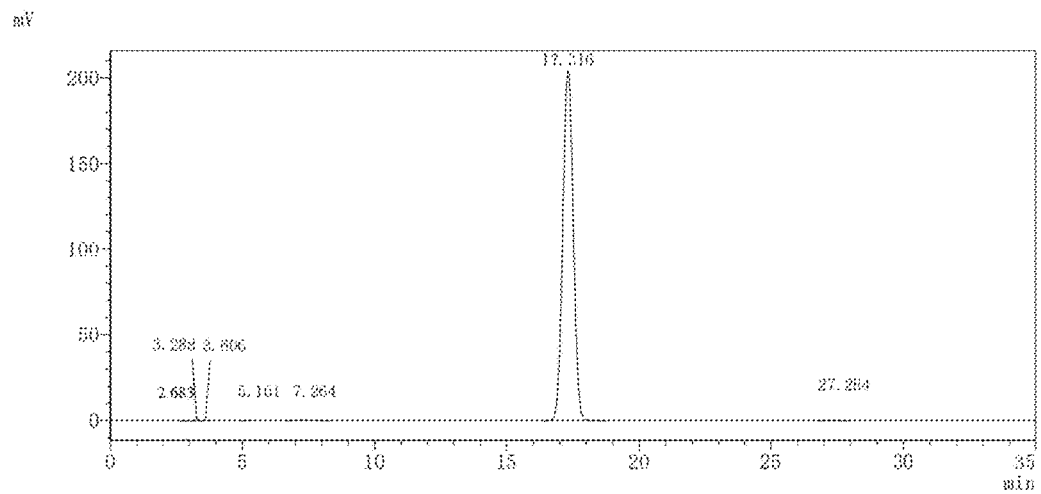

<Peak Table>
Detector A 291nm

| Peak number | Retention time | area | height | theoretical plate number (USP) | Tailing factor | Resolution (USP) | area% |
|---|---|---|---|---|---|---|---|
| 1 | 2.683 | 1297 | 75 | 125 | --- | --- | 0.023 |
| 2 | 3.288 | 6647 | 674 | 2613 | --- | 0.995 | 0.117 |
| 3 | 3.608 | 2509 | 389 | 6860 | --- | 1.470 | 0.044 |
| 4 | 5.161 | 1141 | 81 | 2507 | --- | 5.404 | 0.020 |
| 5 | 7.264 | 17098 | 347 | 470 | --- | 2.400 | 0.302 |
| 6 | 17.316 | 5622532 | 204360 | 8906 | 1.024 | 9.891 | 99.352 |
| 7 | 27.284 | 7991 | 210 | 15122 | --- | 12.295 | 0.141 |
| total | | 5659215 | 206116 | | | | 100.000 |

Dihydromyricetin – 1-48/1-523-1 – Test sample 1-2.lcd

FIG. 2

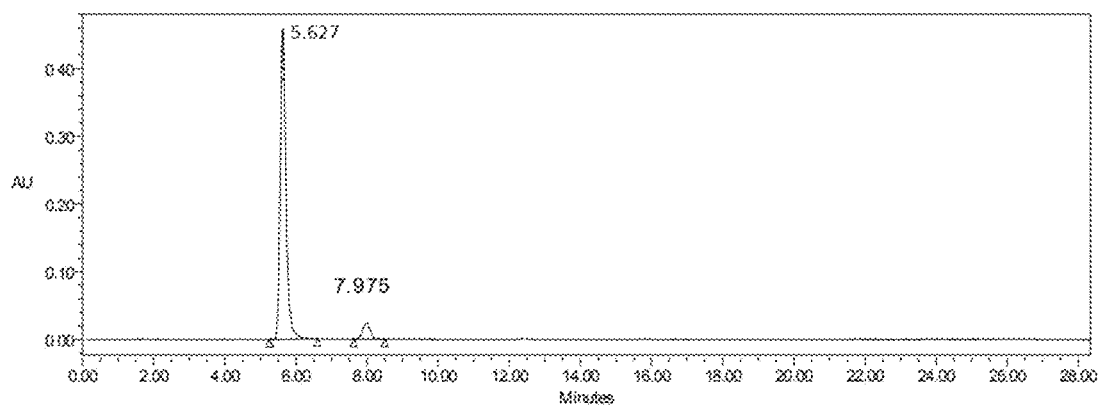
| Peak number | Retention time | area | area% | height | Base peak (m/z) |
|---|---|---|---|---|---|
| 1 | 5.672 | 5300364 | 93.49 | 457256 | 321.28 |
| 2 | 7.975 | 369383 | 6.51 | 24239 | 319.19 |
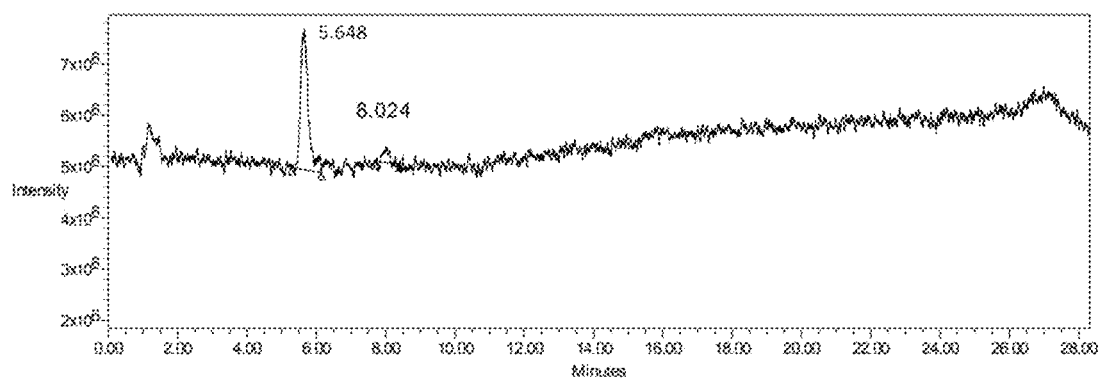
| Peak number | Retention time | area | area% | height | Base peak (m/z) |
|---|---|---|---|---|---|
| 1 | 5.648 | 42327311 | 89.77 | 2747019 | 321.26 |
| 2 | 8.024 | 4822128 | 10.23 | 301668 | 321.32 |
FIG. 3

METHOD FOR EXTRACTING AND SEPARATING DIHYDROMYRICETIN FROM RATTAN TEA

TECHNICAL FIELD

This application relates to the technical field of extraction and separation of natural medicines, in particular to a method for extracting and separating dihydromyricetin from rattan tea.

BACKGROUND OF RELATED ARTS

Dihydromyricetin, also known as vitis, belongs to flavonoid organic compound, molecular formula is $C_{15}H_{12}O_8$, chemical formula is (2R,3R)-3,5,7-trihydroxy-2-(3,4,5-trihydroxyphenyl))benzodihydropyran-4-one, mostly extracted from a woody vine plant of the genus Snake grape in the grape family. The pure product of dihydromyricetin is white needle-like crystals, easily soluble in hot water, ethanol and acetone, slightly soluble in ethyl acetate, insoluble in chloroform and petroleum ether. Studies have shown that dihydromyricetin will undergo an irreversible oxidation reaction at a temperature greater than 100° C. Dihydromyricetin is stable under neutral and slightly acidic conditions. Dihydromyricetin is a special flavonoid compound, and its pharmacological effects have received extensive attention in recent years. In the past ten years, the research literature on dihydromyricetin on anti-tumor, anti-inflammatory, antioxidant, anti-alcohol and liver protection, anti-pathogenic microorganisms, lowering blood sugar, anti-fatigue and regulating blood lipids has been continuously updated. The pharmacological effects of myricetin are continuously studied and the market demand for dihydromyricetin is also increasing.

The scientific name of rattan tea is Snake-toothed grape. It is a kind of vine in the grape family Snake grape genus. It is widely distributed in Hunan, Hubei, Yunnan, Guizhou, Guangdong, Guangxi, Jiangxi and other provinces, concentrated or scattered in 400~1300 m in the mixed forest on the hillside. Rattan tea has a long history of medicinal use, and is effective in treating common symptoms such as sore throat, chronic nephritis, hepatitis, and gastric disease. Analysis of its chemical components revealed that Rattan tea is rich in flavonoids. The total amount of flavonoids in its effective parts can reach up to 40%, and the content of dihydromyricetin monomer can reach about 30%.

At present, the process of extracting dihydromyricetin from rattan tea mainly includes solvent (organic solvent, hot water, lye) extraction, ultrasonic technology extraction, microwave technology extraction, supercritical $CO_2$ extraction, enzymatic extraction, etc. Although the content of dihydromyricetin in the extract obtained through one-step extraction has increased, the content (HPLC) is generally around 60%, which still cannot meet the requirements of the State Food and Drug Administration for traditional Chinese medicine extracts (liquid content of a single component is more than 90%), and part of the extraction process is not suitable for industrial production.

SUMMARY

In view of the above problems, the present application provides a method for extracting and separating dihydromyricetin from rattan tea, which solves the problems of low product purity, complex processes, and unsuitability for industrial production in the prior art.

This application adopts the following technical solutions:

A method for extracting and separating dihydromyricetin from rattan tea, comprising specific steps as follows:

1) weighing rattan tea leaves, then adding solvent thereto, stirring and refluxing extraction, filtering, keeping on refluxing extraction of residue, and combining extract;
2) adding activated carbon to the extract from step 1), performing decolorization, filtering, retaining the filtrate, and then concentrating the filtrate; and
3) crystallizing the concentrated filtrate, filtering, and washing the crystals with cold water and vacuum drying.

Further, in step 1) the volume and dosage of the solvent is 15-20 mL/g based on the mass of rattan tea leaves, each reflux extraction time is 0.5-1 h, and the reflux extraction times are 1-3 times.

Further, the solvent in step 1) is ethanol or methanol solution.

Further, the concentration of the ethanol or methanol solution is 70-80%.

Further, the amount of activated carbon added in step 2) is 20-40% of the mass of the extract in step 1), the decolorization temperature is 40-60° C., the decolorization time is 0.5-1 h, and the filtrate is concentrated to 2-3 times the volume of rattan tea raw material weight.

Further, the crystallization temperature of step 3) is 0-20° C., the crystallization time is 8-12 h, the drying temperature is 60-70° C., and the drying time is 6-8 h.

Further, in step 3) the filtrate comprises isomers of dihydromyricetin as impurities, which are efficiently removed by crystallization.

The above at least one technical solution adopted in this application can achieve the following beneficial effects:

In this process, the dihydromyricetin in rattan tea is initially extracted with the aid of solvent extraction, and the pigment in the extract is removed by decolorization with activated carbon. Finally, due to the fact that dihydromyricetin is hardly soluble in water at room temperature and easily soluble in hot water, the product quality is improved through the purification method of concentration and crystallization, and the liquid content of the obtained dihydromyricetin is more than 90%. The impurity contained in it is the isomer of dihydromyricetin (see FIG. 3), which can be effectively removed by crystallization, and the quality can be well controlled; and its process is simple, the yield is high, it is stable, and it is easy to realize industrialization produce.

BRIEF DESCRIPTION OF THE DRAWINGS

The drawings described here are used to provide a further understanding of the application and constitute a part of the application. The exemplary embodiments and descriptions of the application are used to explain the application and do not constitute an improper limitation of the application. In the attached picture:

FIG. 1 is a liquid chromatogram of Example 1.
FIG. 2 is a liquid chromatogram of Example 2.
FIG. 3 shows the chromatogram of LC/MS.

DETAILED DESCRIPTIONS OF EMBODIMENTS

In order to make the purpose, technical solutions, and advantages of the present application clearer, the technical solutions of the present application will be clearly and completely described below in conjunction with specific embodiments of the present application and the corresponding drawings. Obviously, the described embodiments are only a part of the embodiments of the present application, rather than all the embodiments. Based on the embodiments in this application, all other embodiments obtained by those of ordinary skill in the art without creative work shall fall within the protection scope of this application.

Example 1

500 g rattan tea leaves was weighed and placed in a round-bottomed flask. On the basis of 1 g rattan leaves, 15 mL ethanol was added to 7.5 L 70% ethanol, then stirred and refluxed in a water bath for 0.5 h, filtered and retain the filtrate. The residue is extracted once repeatedly according to the above process. The extract from the two times are combined. Activated carbon was added with 20% to the extract, and the extract was stirred and decolorized at 40° C. for 0.5 h, and filtered to obtain the filtrate. The filtrate was concentrated to 2 times the volume of the raw material weight of rattan tea, transferred to 0-20° C. to crystallize for 8 h, filtered, and washed with a suitable amount of cold water. After vacuum drying at 60° C. for 8 h, 99.0 g of dihydromyricetin was obtained. The yield was 19.8%, and the purity of the product was 99.6%. The liquid chromatogram is shown in FIG. 1.

Example 2

600 g rattan tea leaves was weighed and placed in a round-bottomed flask. On the basis of 1 g rattan leaves, 20 mL ethanol was added to 12 L 75% ethanol, then stirred and refluxed in a water bath for 45 min. The residue is extracted twice repeatedly according to the above process. The extract from the three times are combined. Activated carbon was added with 30% to the extract, and the extract was stirred and decolorized at 50° C. for 45 min, and filtered to obtain the filtrate. The filtrate was concentrated to 2.5 times the volume of the raw material weight of rattan tea, transferred to 0-20° C. to crystallize for 10 h, filtered, and washed with a suitable amount of cold water. After vacuum drying at 65° C. for 7 h, 112.0 g of dihydromyricetin was obtained. The yield was 18.7%, and the purity of the product was 99.4%. The liquid chromatogram is shown in FIG. 2.

Example 3

700 g rattan tea leaves was weighed and placed in a round-bottomed flask. On the basis of 1 g rattan leaves, 20 mL ethanol was added to 14 L 80% ethanol, then stirred and refluxed in a water bath for 1 h. The residue is extracted once repeatedly according to the above process. The extract from the two times are combined. Activated carbon was added with 40% to the extract, and the extract was stirred and decolorized at 60° C. for 1 h, and filtered to obtain the filtrate. The filtrate was concentrated to 3 times the volume of the raw material weight of rattan tea, transferred to 0-20° C. to crystallize for 12 h, filtered, and washed with a suitable amount of cold water. After vacuum drying at 70° C. for 6 h, 115.0 g of dihydromyricetin was obtained. The yield was 16.4%, and the purity of the product was 99.5%.

Example 4

500 g rattan tea leaves was weighed and placed in a round-bottomed flask. On the basis of 1 g rattan leaves, 16 mL ethanol was added to 16 L 70% ethanol, then stirred and refluxed in a water bath for 0.8 h. The residue is extracted once repeatedly according to the above process. The extract from the two times are combined. Activated carbon was added with 30% to the extract, and the extract was stirred and decolorized at 45° C. for 0.6 h, and filtered to obtain the filtrate. The filtrate was concentrated to 2 times the volume of the raw material weight of rattan tea, transferred to 0-20° C. to crystallize for 9 h, filtered, and washed with a suitable amount of cold water. After vacuum drying at 60° C. for 7 h, 104.0 g of dihydromyricetin was obtained. The yield was 20.8%, and the purity of the product was 99.3%.

High performance liquid chromatography (HPLC) determination conditions:
Instrument: Shimadzu High Performance Liquid Chromatograph LC-20A (with SIL-20A autosampler and Labsolution DB workstation)
Column: Angilent-TC C18, 250 mm×4.6 mm, 5 um
Wavelength: 291 nm
Injection volume: 10 uL The above descriptions are only examples of the present application, and are not used to limit the present application. For those skilled in the art, this application can have various modifications and changes. Any modification, equivalent replacement, improvement, etc. made within the spirit and principle of this application shall be included in the scope of the claims of this application.

What claimed is claimed:

1. A method for extracting and separating dihydromyricetin from rattan tea, characterized by comprising steps are as follows:
   1) weighing rattan tea leaves, then adding solvent thereto, stirring and reflux extracting, filtering, keeping on reflux extracting residue, and combining extract;
   2) adding activated carbon to the extract from step 1), performing decolorization, filtering, retaining the filtrate, and then concentrating the filtrate; and
   3) crystallizing the concentrated filtrate from step 2), filtering, and washing the crystals with cold water and vacuum drying;
   wherein the crystallization temperature of step 3) is 0-20° C., the crystallization time is 8-12 h, the drying temperature is 60-70° C., and the drying time is 6-8 h.

2. The method according to claim 1, wherein in step 1) the volume and dosage of the solvent is 15-20 mL/g based on the mass of rattan tea leaves, each reflux extraction time is 0.5-1 h, and the number of the reflux extractions is 1-3.

3. The method according to claim 2, wherein the solvent in step 1) is ethanol or methanol solution.

4. The method of claim 3, wherein the concentration of the ethanol or methanol solution is 70-80%.

5. The method according to claim 1, wherein the amount of activated carbon added in step 2) is 20-40% of the mass of the extract in step 1), the decolorization temperature is 40-60° C., the decolorization time is 0.5-1 h, and the volume of the filtrate is concentrated to 2-3 times the weight of the rattan tea leaves.

6. The method according to claim 1, wherein in step 3) the filtrate comprises isomers of dihydromyricetin as impurities, which are efficiently removed by crystallization.

* * * * *